US009574986B2

(12) United States Patent
Janka

(10) Patent No.: US 9,574,986 B2
(45) Date of Patent: Feb. 21, 2017

(54) APPARATUS AND PROCESS FOR PRODUCING ACKNOWLEDGED AIR FLOW AND THE USE OF SUCH APPARATUS IN MEASURING PARTICLE CONCENTRATION IN ACKNOWLEDGED AIR FLOW

(71) Applicant: Pegasor Oy, Tampere (FI)

(72) Inventor: Kauko Janka, Tampere (FI)

(73) Assignee: Pegasor Oy, Tampere (FI)

( * ) Notice: Subject to any disclaimer, the term of this patent is extended or adjusted under 35 U.S.C. 154(b) by 43 days.

(21) Appl. No.: 14/379,676

(22) PCT Filed: Feb. 7, 2013

(86) PCT No.: PCT/FI2013/050135
§ 371 (c)(1),
(2) Date: Aug. 19, 2014

(87) PCT Pub. No.: WO2013/121094
PCT Pub. Date: Aug. 22, 2013

(65) Prior Publication Data
US 2015/0192508 A1    Jul. 9, 2015

(30) Foreign Application Priority Data

Feb. 18, 2012 (FI) ..................................... 20125187

(51) Int. Cl.
*G01N 15/06* (2006.01)
*H01T 23/00* (2006.01)
*G01N 15/00* (2006.01)

(52) U.S. Cl.
CPC .......... *G01N 15/06* (2013.01); *G01N 15/0656* (2013.01); *H01T 23/00* (2013.01); *G01N 2015/0026* (2013.01)

(58) Field of Classification Search
CPC ..... G01N 15/06; G01N 15/0656; H01T 23/00; H01T 19/00; H01T 19/02; H01T 19/04; G01F 1/56; G01F 1/64
See application file for complete search history.

(56) References Cited

U.S. PATENT DOCUMENTS 3,945,251 A * 3/1976 Pierce .................... G01F 1/64
73/861.09
2005/0083633 A1  4/2005 Riebel et al.
(Continued)

FOREIGN PATENT DOCUMENTS

WO   WO-2004/113904 A1   12/2004
WO   WO-2006/127803 A2   11/2006
WO   WO-2009/109688 A1    9/2009

OTHER PUBLICATIONS

International Search Report and Written Opinion, corresponding International Application No. PCT/FI2013/050135, May 2, 2013 mailing date.

*Primary Examiner* — Blake A Tankersley
(74) *Attorney, Agent, or Firm* — Marshall, Gerstein & Borun LLP

(57) ABSTRACT

Apparatus (1) for generating acknowledged flow (Q), comprising a first passage (2) with ends (3,4) for acknowledged flow (Q) inlet and outlet, a discharge electrode (5) for generating airborne unipolar ions (8) positioned inside the first passage (2), a counter electrode (6) adapted to attract said airborne ions (8), thereby being adapted to cause a net flow (7) of airborne ions (8) and thereby generating an airflow (Q) in the direction of the net flow of airborne ions (8), sensing element (12, 13), the output of which is a function of the concentration of the airborne electric charge (8, 11), means (17) for switching or modulating a parameter which affects the output of the sensing element (12,13) and means for determining the volumetric flow (Q) on the basis of the time response which switching or modulation creates to the sensing element (12,13) output. 11. Use of apparatus (Continued)

Figure 1:
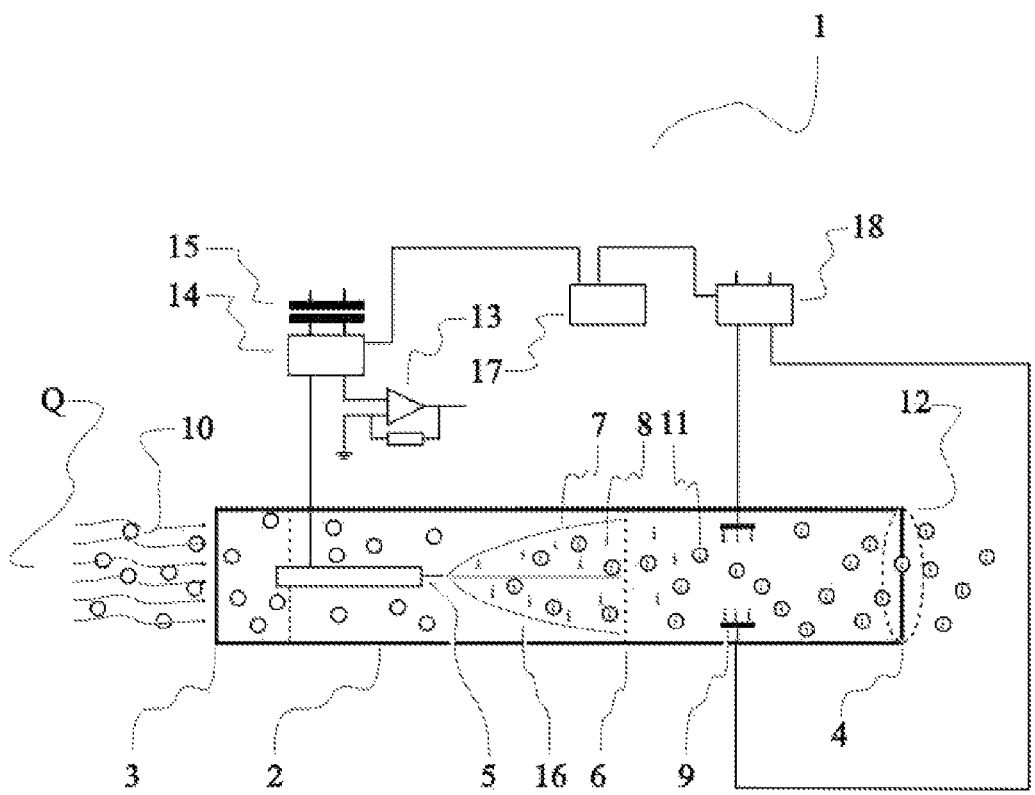

(1) as described in the previous claims for determining ultrafine particle concentration. Process for generating acknowledged flow.

11 Claims, 2 Drawing Sheets

(56) References Cited

U.S. PATENT DOCUMENTS

| | | |
|---|---|---|
| 2011/0216317 A1 | 9/2011 | Marra |
| 2011/0299214 A1 | 12/2011 | Gefter et al. |
| 2013/0153762 A1* | 6/2013 | Munchmeyer ......... G01N 27/64 250/282 |

* cited by examiner

APPARATUS AND PROCESS FOR PRODUCING ACKNOWLEDGED AIR FLOW AND THE USE OF SUCH APPARATUS IN MEASURING PARTICLE CONCENTRATION IN ACKNOWLEDGED AIR FLOW

The present invention relates to an apparatus for producing a known air flow. The present invention also relates to a process for producing a known air flow. The present further relates to the use of the apparatus for producing a known air flow in determining particle concentration in the flow.

BACKGROUND OF THE INVENTION

Within various sensors for measuring air quality there is a need to pass air through the sensor with a known volumetric flow. Such sensors include e.g. particle concentration sensors, humidity sensors and various gas sensors.

Fine particles are formed in many industrial processes and combustion processes. Furthermore, fine particles exist in breathing air flowing in ducts and ventilation systems and in room spaces. For various reasons these fine particles are measured. The fine particle measurements may be conducted because of their potential health effects and also for monitoring operation of industrial processes and combustion processes. The fine particles are also measured in ventilation systems for monitoring air quality. Another reason for monitoring fine particles is the increasing use and production of nanosized particles in industrial processes.

One prior art method and apparatus for measuring fine particles is described in document WO2009109688 A1. In this prior art method clean, essentially particle free, gas is supplied into the apparatus and directed as a main flow via an inlet chamber to an ejector provided inside the apparatus. The clean gas is further ionized before and during supplying it into the inlet chamber. The ionized clean gas may be preferably fed to the ejector at a sonic or close to sonic speed. The ionizing of the clean gas may be carried out for example using a corona charger. The inlet chamber is further provided with a sample inlet arranged in fluid communication with a channel or a space comprising aerosol having fine particles. The clean gas flow and the ejector together cause suction to the sample inlet such that a sample aerosol flow is formed from the duct or the space to the inlet chamber. The sample aerosol flow is thus provided as a side flow to the ejector. The ionized clean gas charges the particles. The charged particles may be further conducted back to the duct or space containing the aerosol. The fine particles of the aerosol sample are thus monitored by monitoring the electrical charge carried by the electrically charged particles. Free ions may further be removed by using an ion trap.

Operation of the particle sensor described in WO2009109688 A1 requires a clean air or gas source. Although in some special cases where the measurement interval is short a gas cylinder or equivalent can be used to provide the clean air, it is in most cases convenient to use some sort of a pump which is able to generate the required volumetric flow and operation pressure. When all the parameters stay essentially constant the construction described in WO2009109688 A1 provides an essentially constant sample flow through the sensor. However, if changes in operational parameters or other conditions may occur, such as changes in particle accumulation in the sensor, the volumetric flow through the sensor should be determined. WO2009109688 A1 is, however, silent on this.

One important demand for the fine particle monitoring apparatuses is reliable operation and efficient operation. Furthermore, it is also preferable that these fine particle monitoring apparatuses may be operated with low energy consumption and continuously for conducting fine particle measurements in real-time.

Whilst there exists conventional ways for generating the flow required for the operation of the sensors, such as fans, pumps or use of compressed gas, such solutions are sometimes not convenient due to e.g. frequently required maintenance. Thus there is a need for flow generation in a way which provides a long-term, reliable air flow.

U.S. Pat. No. 4,210,847, The United States of America as represented by the Secretary of the Navy, Jan. 7, 1980, provides a device for generating an air jet without the use of moving parts. High voltage is used to create a corona discharge electric wind in a ducted, compact, portable generator that can be used for augmentation cooling applications where high voltage is available.

The idea of using a corona discharge electric wind (also called "ion wind", "ionic wind" or "corona wind") in a sensor is provided in United States Patent Application Publication US 2011/0216317, Koninklijke Philips Elelctronics N.V., Aug. 9, 2011, describing a sensor which comprises a high-voltage discharge electrode for generating airborne unipolar ions that charge the airborne particles in the airflow. The generated ions are furthermore used to set-up an ionic wind between the discharge electrode and a counter electrode inside the sensor. The ionic wind is the driving force for maintaining the airflow through the sensor and allows sensor operation to occur free of audible noise. The presence of charged particles in the airflow is measured by an electrical current meter in the particle sensing section which measures the particle-bound charge that precipitates per unit time on the surface of a precipitation electrode after all airborne ions have been removed from air by a separate screening electrode positioned upstream of the particle sensing section.

Although the ion wind generated by a corona discharge unit may stay stable with clean air and with short time intervals, there is a tendency for the ion wind to change due to changes in corona geometry or corona tip soiling.

U.S. Pat. No. 3,324,291, Xerox Corporation, Jun. 6, 1967, describes the use of corona wind in a copying machine for generating an air flow which is utilized to provide a cleansing action by preventing the accumulation or deposition of dust in or about the unit. To ensure that the air entering the unit is itself generally free of dust or dirt particles likely to accumulate, there is provided a filter upstream of the corona wind generating unit. This will keep the air clean but while the filter gets loaded with dust, the pressure drop across the filter increases thus reducing the flow generated due to the ionic wind.

Even if the blocking filter problem might be solved by using an electrostatic precipitator, there still exists the feature that the air flow generated by an electric wind is usually quite low and due to small pressure differences e.g. flow through a sensor is sensitive to disturbances created by the sensor environment. Thus there exists a need for improved generation of known (i.e. identified) air flow using electric wind.

BRIEF DESCRIPTION OF THE INVENTION

The preferred embodiments of the invention are disclosed in the dependent claims.

The inventor has surprisingly found a method which will solve the prior art problems described above, with low-cost flow measurement or monitoring. The low-cost flow measurement or monitoring has been described in detail in applicant's currently non-public PCT application PCT/FI2011/050730, which is hereby incorporated by reference in its entirety.

The invented process for generating acknowledged flow comprises generating airborne unipolar ions with a discharge electrode in a passage, using a counter electrode adapted to attract said airborne ions to cause a net flow of airborne ions and thereby generating an airflow in the direction of the net flow of airborne ions, determining concentration of airborne electric charge, switching or modulating a parameter which affects the concentration of airborne electric charge and determining the volumetric flow on the basis of the time response which switching or modulation creates to the concentration of airborne electric charge. Preferably a corona needle is used for generating airborne unipolar ions.

There are only a limited number of switchable parameters which may affect the concentration measurement result of a particle sensor based on unipolar ion generation. Typically the advantageous parameters to switch or modulate are the particle charging efficiency and particle trapping and the actual means to modulate are the corona voltage/current and ion trap voltage.

The acknowledged flow may be divided between first passage and second passage where the second passage is placed inside the first passage. Particles entering the second passage are essentially removed, particle removal being carried out upstream of the discharge electrode. By this way a small, essentially particle-free air flow is passed next to the corona needle and thus the tip of the corona needle is not soiled. The first and second passages are preferably constructed in such a way that the flow through the second passage is less than 10%, preferably less than 5% and more preferably less than 2% of the total flow and thus the use of a second passage with particle removal will not create a considerable measurement error even when the acknowledged flow generating apparatus is used with particle measurement sensors. The flows of the first and second passage are combined in the third passage which also works as a mixing channel for ions and particles when the apparatus for acknowledged flow generation is used in particle measurement sensors based on particle charging, such as described e.g. in described in document WO2009109688 A1.

In one embodiment of the present invention, the invented process comprises electrically charging at least a fraction of particles entering the acknowledged flow generating apparatus, measuring the electrical current carried by charged particles; and switching or modulating the electrical discharge unit at least between first charging stage where the electrical discharge electrode provides a first charge amount to at least a fraction of particles and second charging stage where the electrical discharge electrode provides a second charge amount to at least a fraction of particles.

In the preferred embodiment of the present invention the response from the switched or modulated mode of the electrical discharge unit is determined by synchronic detection. Synchronic detection can be realized by using either analogue electronics or digitally. The digital realization can obviously be carried out in a separate computing unit or it may be integrated to a common controller or computing unit, where other control functions of the electrical impactor are carried out as well.

In another embodiment of the present invention, the invented process comprises electrically charging at least a fraction of the particles entering the acknowledged flow generating apparatus, measuring the electrical current carried by the charged particles, removing ions, charged ultrafine particles or charged fine particles from the aerosol passing through the apparatus and switching or modulating the ion/particle trap at least between OFF-mode where the ion/particle trap essentially removes free ions and ON-mode where ion/particle trap essentially removes particles having a diameter smaller than $d_p$. Free ion or particle removal is dependent on the strength of the electrical field across the ion trap.

The invented process comprises determining the essential parameters of the transfer function of the acknowledged flow generating apparatus and using these essential parameters to calculate the volumetric flow through the apparatus. In one embodiment of the present invention, the invented process comprises providing a computational reference signal, comparing the sensing element output to the reference signal, adjusting the reference signal for maximum correlation between the sensing element output and the reference signal, computing the transfer function of apparatus from the reference signal with maximum correlation and determining the volumetric flow through apparatus using at least some parameters of the computed transfer function. The computational reference signal may follow at least a first-order low-pass filter, in which case determining the delay time $t_d$ and time constant $\tau$ the first-order low-pass filter allows determining the volumetric flow through apparatus using the inverse of $t_d$, $\tau$ or the sum thereof, $t_d+\tau$.

In the invented process the switching/modulation frequency of a parameter affecting the sensing element output may between 0.01 Hz and 10 Hz, thus providing a fast determination of the acknowledged flow and thus providing accurate basis for sensors where air flow through the sensor is required.

The essential parameters can be determined even continuously when required e.g. due to rapidly changing aerosol composition. If the changes in the measurement environment are not remarkable on a short time interval, and when the maximum time response of the measurement is required, the determination of the essential parameters may be carried out with longer intervals.

BRIEF DESCRIPTION OF THE FIGURES

In the following the invention will be described in greater detail, in connection with preferred embodiments, with reference to the attached drawings, in which FIG. 1 is a schematic view of one embodiment of an apparatus according to the present invention; and FIG. 2 is a schematic view of another embodiment of an apparatus according to the present invention.

DETAILED DESCRIPTION OF THE INVENTION

FIG. 1 shows the invented apparatus 1 for generating acknowledged flow Q. Apparatus 1 comprises a first passage 2 with ends 3, 4 for the inlet and outlet of the acknowledged flow Q. The first passage 2 is preferably designed so that it generates a pressure difference of less than 20 Pa with the documented flow Q, more preferably less than 10 Pa and most preferably less than 5 Pa, as such pressure levels can be typically achieved by using electric wind to generate flow. In most cases the ends 3, 4 of the first passage 2 are essentially free. Inside passage 2 is a discharge electrode 5 powered from a high voltage source 14, which is isolated from mains with an isolation transformer 15. Discharge electrode 5 is adapted for generating airborne unipolar ions 8 and a counter electrode 6 is adapted to attract said airborne ions 8, thereby being adapted to cause a net flow 7 of airborne ions 8 and thereby generating an airflow Q in the direction of the net flow of airborne ions 8. Apparatus 1 further comprises sensing element 12, 13, the output of which is a function of the concentration of the airborne electric charge 8, 11. The sensing element may be constructed as measuring the charge entering or passing a sensing element 12, or it may be constructed as an electrometer, which measures the electric current escaping from apparatus 1 as airborne electric charge. This so called "escaping current technique" for measuring particle concentration is described in detail in WO2009109688 A1, which is hereby incorporated by reference in its entirety. Apparatus 1 further comprises means 17 for switching or modulating a parameter which affects the output of the sensing element 12, 13 and means (not shown in FIG. 1) for determining the volumetric flow Q on the basis of the time response which switching or modulation creates to the sensing element 12,13 output. Preferably the volumetric flow Q is determined by providing a computational reference signal, comparing the sensing element 12, 13 output to the reference signal, adjusting the reference signal for maximum correlation between the sensing element 12, 13 output and the reference signal, computing the transfer function of apparatus 1 from the reference signal with maximum correlation and determining the volumetric flow Q through apparatus 1 using at least some parameters of the computed transfer function. In one embodiment of the present invention, the computational reference signal may follow at least a first-order low-pass filter, in which case determining the delay time $t_d$ and time constant P of the first-order low-pass filter allows determining the volumetric flow Q through apparatus 1 using the inverse of $t_d$, $\tau$ or the sum thereof, $t_d+\tau$.

Figure 2:
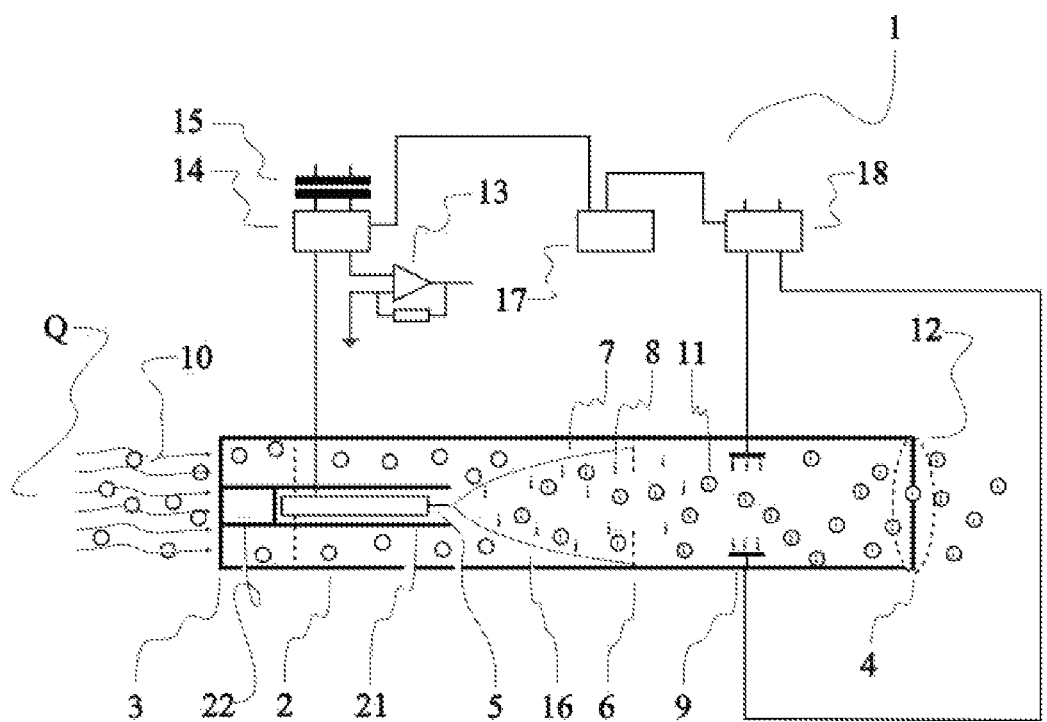

In one embodiment of the present invention, apparatus 1 comprises a corona needle adapted to work as the discharge electrode 5. To avoid corona needle soiling, apparatus 1 comprises in one embodiment of the present invention, shown in FIG. 2, a second passage 21 placed inside the first passage 2. The second passage comprises a particle removal unit 22 placed upstream of the discharge electrode 5. As the ion wind drags air into apparatus 1, a fraction of the air flow Q passes through filter 22 and particles are essentially removed from this flow fraction. Clean air then passes through second passage 21 and from the vicinity of corona needle 5, thus preventing the corona needle from soiling. As the fraction of the flow passing through passage 21 is small compared to the flow passing through passage 2, the use of such arrangement does not lead to harmfully erroneous results even when apparatus 1 is used to generate acknowledged flow for a particle measurement sensor. A surprising finding is that the flow of the ion wind does not follow the clean-air from the second passage 21. In that case the flow feeding force would direct mainly to the said clean-air flow and not to the flow from the first passage 2, thus feeding mainly clean-air flow from passage 21. The flow velocities in this kind of arrangements are too low to generate turbulent mixing. But, according to the finding the ion cloud from the passage 21 spreads effectively due to the electrostatic attraction to the whole cross section of the flow channel, where the flows of passage 2 and 21 have joined. For this reason the force caused by electrostatic field to the ions is directed to the whole cross section of flow channel, respectively. This feature enables also the particles passing from the passage 2 to be charged electrically by ions fed from the second passage 21. In order to enhance air withdrawal from passage 2, the counter electrode 6 is designed in such a way that the net flow 7 of airborne ions 8 is directed from the corona needle 5 towards the counter electrode 6, which essentially does not cover the straight flow direction from passage 21 towards end 4 of apparatus 1.

In one embodiment of the present invention, apparatus 1 comprises a charging chamber 16 placed downstream the discharge electrode 5 for electrically charging at least a fraction of particles 10 entering apparatus 1 with the acknowledged flow Q, an ion/particle trap 9 for removing ions 8 which are not attached to particles 10, means 12, 13 for measuring the electrical current carried by charged particles 11 and means 17 for switching or modulating the electrical discharge unit 5 at least between first charging stage where the electrical discharge electrode 5 provides a first charge amount to at least a fraction of particles 10 and second charging stage where the electrical discharge electrode 5 provides a second charge amount to at least a fraction of particles 10. This embodiment provides the benefit that as the charged particles are more difficult to remove from the air stream Q than the ions (free charges) 8, the response to the modulation of the electrical discharge unit 5 is more accurate. The electrical discharge unit may be switched between ON and OFF stages only, in which case the volumetric flow is easily determined from the response of switching to ON stage only, by knowing the volume between the corona discharge unit 5 and the sensing unit 12, or when the escaping current technique with sensing element 13 is used, the distance between the corona discharge unit 5 and the output end 4 of apparatus 1. In another embodiment the electrical discharge unit 5 is modulated between at least two voltages (and/or between two discharging currents), each of which provides an air flow through apparatus 1.

In another embodiment of the present invention apparatus 1 comprises a charging chamber 16 placed downstream said discharge electrode 5 for electrically charging at least a fraction of the particles 10 entering apparatus 1, means 12, 13 for measuring the electrical current carried by the charged particles 11, an ion/particle trap 9 for removing ions 8, and/or charged particles 11 having a diameter smaller than $d_p$ and means 17 for switching or modulating the ion/particle trap 9 power source 18 output at least between OFF-mode where the ion/particle trap 9 essentially removes free ions 8 and ON-mode where ion/particle trap 9 essentially removes charged particles 11 having a diameter smaller than $d_p$. The advantage of such embodiment is that the flow Q can be kept essentially constant throughout the flow determination.

In one embodiment of the present invention, apparatus 1 comprises means for determining the essential parameters of the transfer function of apparatus 1. These means may be constructed by analogue or digital means as obvious for a person skilled in the art and the means may be realized within one or several functional blocks.

In one embodiment of the present invention, apparatus 1 comprises means for providing a computational reference signal and the signal is connected to the means for switching or modulating a parameter essentially affecting the sensing element output. Apparatus 1 further comprises means for comparing the sensing element output to the reference signal, means for adjusting the reference signal for maximum correlation between the sensing element output and the reference signal, means for computing the transfer function of apparatus 1 from the reference signal with maximum correlation and means for determining the volumetric flow Q through apparatus 1 using at least some parameters of the computed transfer function. In the preferred embodiment apparatus 1 comprises means for providing a computational reference signal following at least a first-order low-pass filter, means for determining the delay time $t_d$ and time constant $\tau$ of the first-order low-pass filter and means for determining the volumetric flow through apparatus 1 using the inverse of $t_d$, $\tau$ or the sum thereof, $t_d+\tau$. It is obvious for a person skilled in the art that other dynamic models than the sum of delay and mixed reactor can be used, depending on flow behaviour inside the device.

In one embodiment of the present invention, apparatus 1 comprises means for adjusting the switching/modulation frequency of the means 17 for switching or modulating a parameter which affects the output of the sensing element 12,13, between 0.01 Hz and 10 Hz. Such embodiment offers a fast flow determination.

The present invention also includes use of apparatus 1 as described in the previous embodiments for determining ultrafine particle concentration. Such use of apparatus 1 comprises determining cumulative flow $Q_t$ for the period of time t on the basis of the time response which switching or modulation creates to the sensing element output, determining the cumulative particle mass $M_t$ or cumulative number of particles $N_t$ for the period of time t and determining particle mass or number concentration, M or N, by dividing cumulative particle mass $M_t$ or cumulative number of particles $N_t$ by the cumulative flow $Q_t$, i.e. $M=M_t/Q_t$ and $N=N_t/Q_t$. A significant advantage of the arrangement described above is that the most expensive components; sensing elements and discharge units, are common for both functions; controlled flow generation and particle concentration sensing.

It is apparent to a person skilled in the art that as technology advanced, the basic idea of the invention can be implemented in various ways. The invention and its embodiments are therefore not restricted to the above examples, but they may vary within the scope of the claims.

The invention claimed is:

1. Process for generating acknowledged flow, comprising:
   a. generating airborne unipolar ions with a discharge electrode in a passage;
   b. using a counter electrode adapted to attract said airborne ions to cause a net flow of airborne ions and thereby generating an airflow in the direction of the net flow of airborne ions;
   c. determining concentration of airborne electric charge;
   d. switching or modulating a parameter which affects the concentration of airborne electric charge; and
   e. determining the volumetric flow on the basis of the time response which switching or modulation creates to the concentration of airborne electric charge.

2. Process of claim 1, comprising using a corona needle for generating airborne unipolar ions.

3. Process of claim 1, in which the passage comprises a first passageway and a second passageway, the process comprising dividing the acknowledged flow between the first passageway and the second passageway.

4. Process as in claim 3, comprising removing particles entering the second passageway, particle removal being carried out upstream of the discharge electrode.

5. Process as in claim 3, in which the passage comprises a third passageway, the process comprising combining the flows of the first passageway and the second passageway in the third passageway.

6. Process as in claim 1, in which:
   the step of generating airborne unipolar ions comprises electrically charging at least a fraction of particles entering an apparatus;
   the step of determining concentration of airborne electric charge comprises measuring the electrical current carried by charged particles; and
   the step of switching or modulating a parameter comprises switching or modulating the electrical discharge unit at least between first charging stage where the electrical discharge electrode provides a first charge amount to at least a fraction of particles and second charging stage where the electrical discharge electrode provides a second charge amount to at least a fraction of particles.

7. Process as in claim 1, comprising in which:
   the step of generating airborne unipolar ions comprises electrically charging at least a fraction of the particles entering an apparatus;
   the step of determining concentration of airborne electric charge comprises measuring the electrical current carried by the charged particles;
   the process comprises removing ions, charged ultrafine particles or charged fine particles from the aerosol passing through the apparatus; and
   the step of switching or modulating a parameter comprises switching or modulating the ion/particle trap at least between OFF-mode where the ion/particle trap essentially removes free ions and ON-mode where ion/particle trap essentially removes particles having a diameter smaller than $d_p$.

8. Process as in claim 1, comprising determining the essential parameters of the transfer function of an apparatus.

9. Process as in claim 8, in which the step of determining the volumetric flow comprises:
   a. providing a computational reference signal;
   b. comparing the sensing element output to the reference signal;
   c. adjusting the reference signal for maximum correlation between the sensing element output and the reference signal;
   d. computing the transfer function of an apparatus from the reference signal with maximum correlation; and
   e. determining the volumetric flow through the apparatus using at least some parameters of the computed transfer function.

10. Process as in claim 9, in which the step of determining the volumetric flow comprises:
    a. providing a computational reference signal following at least a first-order low-pass filter;
    b. determining the delay time $t_d$ and time constant $\tau$ of the first-order low-pass filter; and
    c. determining the volumetric flow through an apparatus (1) using the inverse of $t_d$, $\tau$ or the sum thereof, $t_d+\tau$.

11. Process as in claim 1, comprising adjusting the switching/modulation frequency of a parameter affecting the sensing element output, between 0.01 Hz and 10 Hz.

* * * * *

UNITED STATES PATENT AND TRADEMARK OFFICE
CERTIFICATE OF CORRECTION

Page 1 of 1

PATENT NO. : 9,574,986 B2
APPLICATION NO. : 14/379676
DATED : February 21, 2017
INVENTOR(S) : Kauko Janka It is certified that error appears in the above-identified patent and that said Letters Patent is hereby corrected as shown below:

In the Claims

At Column 8, Line 17, "comprising in which" should be -- in which --.

At Column 8, Lines 55-56, "apparatus (1)" should be -- apparatus --.

Signed and Sealed this
Fifteenth Day of August, 2017

Joseph Matal
*Performing the Functions and Duties of the*
*Under Secretary of Commerce for Intellectual Property and*
*Director of the United States Patent and Trademark Office*